(12) United States Patent
Vendelbo

(10) Patent No.: US 11,863,974 B2
(45) Date of Patent: *Jan. 2, 2024

(54) METHOD FOR HEARING SYSTEM COMMUNICATION AND RELATED DEVICES

(71) Applicant: GN Hearing A/S, Ballerup (DK)

(72) Inventor: Allan Munk Vendelbo, Ballerup (DK)

(73) Assignee: GN HEARING A/S, Ballerup (DK)

( * ) Notice: Subject to any disclaimer, the term of this patent is extended or adjusted under 35 U.S.C. 154(b) by 505 days.

This patent is subject to a terminal disclaimer.

(21) Appl. No.: 16/953,306

(22) Filed: Nov. 19, 2020

(65) Prior Publication Data
US 2021/0076199 A1    Mar. 11, 2021

Related U.S. Application Data

(63) Continuation of application No. 15/811,678, filed on Nov. 14, 2017, now Pat. No. 10,952,070.

(30) Foreign Application Priority Data

Dec. 8, 2016  (EP) ..................................... 16202919

(51) Int. Cl.
*H04W 12/033*   (2021.01)
*H04R 25/00*    (2006.01)
(Continued)

(52) U.S. Cl.
CPC .......... *H04W 12/033* (2021.01); *G06F 21/44* (2013.01); *G06F 21/64* (2013.01); *G16H 40/67* (2018.01);
(Continued)

(58) Field of Classification Search
CPC . H04W 12/033; H04W 12/106; H04W 12/33; H04L 9/0618; H04L 9/16;
(Continued)

(56) References Cited

U.S. PATENT DOCUMENTS 10,027,474 B2 * 7/2018 Pedersen ............... H04L 9/0822
10,510,446 B2 * 12/2019 Westermann .......... G16H 10/65
(Continued)

FOREIGN PATENT DOCUMENTS

EP         3032857         6/2016
EP         3032857 A1      6/2016
(Continued)

OTHER PUBLICATIONS

"Design and implementation of a hearing aid system based on Android platform" (Wanfang, Xilong Zhang, May 30, 2018).
(Continued)

*Primary Examiner* — Han Yang
(74) *Attorney, Agent, or Firm* — Vista IP Law Group, LLP

(57) ABSTRACT

A method for communication in a hearing system comprising the server device and a hearing device system, the hearing device system comprising a hearing device and a user accessory device with a user application installed thereon, the method includes: obtaining hearing device data for the hearing device; securing the hearing device data using a first security scheme to obtain a first output; securing the first output using a second security scheme to obtain a second output, wherein the second security scheme is different from the first security scheme; and transmitting the second output to the user accessory device.

46 Claims, 4 Drawing Sheets

(51) Int. Cl.

| | |
|---|---|
| *G16H 40/67* | (2018.01) |
| *G06F 21/44* | (2013.01) |
| *G06F 21/64* | (2013.01) |
| *H04L 9/06* | (2006.01) |
| *H04L 9/16* | (2006.01) |
| *H04L 9/32* | (2006.01) |
| *H04L 9/40* | (2022.01) |
| *H04W 12/106* | (2021.01) |

(52) U.S. Cl.
CPC ............ *H04L 9/0618* (2013.01); *H04L 9/16* (2013.01); *H04L 9/3247* (2013.01); *H04L 63/0428* (2013.01); *H04R 25/70* (2013.01); *H04L 2209/80* (2013.01); *H04L 2209/88* (2013.01); *H04R 2225/55* (2013.01); *H04W 12/106* (2021.01)

(58) Field of Classification Search
CPC ............ H04L 9/3247; H04L 63/0428; H04L 2209/80; H04L 2209/88; H04R 25/70; H04R 2225/55; G06F 21/44; G06F 21/64; G16H 40/67
See application file for complete search history.

(56) References Cited

U.S. PATENT DOCUMENTS

| | | | |
|---|---|---|---|
| 2010/0174909 A1 | 7/2010 | Ashdown | |
| 2014/0211973 A1 | 7/2014 | Wang et al. | |
| 2016/0173278 A1* | 6/2016 | Pedersen | ............ H04L 63/1483 380/255 |
| 2017/0006029 A1* | 1/2017 | Pedersen | ............ H04W 12/50 |

FOREIGN PATENT DOCUMENTS

| | | |
|---|---|---|
| GB | 2411554 | 8/2005 |
| GB | 2411554 A | 8/2005 |
| JP | 2013-162433 | 8/2013 |
| JP | 2014-506047 | 3/2014 |
| JP | 2015-233173 | 12/2015 |
| JP | 2015233173 A * | 12/2015 |
| JP | 2016-136718 | 7/2016 |
| WO | WO 2016/078709 | 5/2016 |

OTHER PUBLICATIONS

Office Action for Chinese patent application No. 201711120783.7 dated Dec. 13, 2021.
European Search Report for EP Patent Appln. No. 16202919 dated Feb. 16, 2017.
Foreign Office Action for Japanese patent application No. 2017-232954 dated Oct. 21, 2021 (with English translation).
Keisuke Takemori "Key managements for ECU and Code authentications using tamper-resistant secure element, IEICE technical report, Japan, The institute of Electronics, Information and Communication Engineers, Dec. 10, 2015, vol. 115, No. 366, p. 227-232".
Kazuyuki Nagaya "Minnade Chosen! Network specialist exam IPsec and SSL", Nikkei Network, Japan Nikkei BP company, Dec. 28, 2008, published in Jan. 2009 (No. 105), p. 98-102.
Non-Final Office Action for U.S. Appl. No. 15/811,678 dated Aug. 9, 2019.
Final Office Action for U.S. Appl. No. 15/811,678 dated Mar. 11, 2020.
Amendment Response to NFOA for U.S. Appl. No. 15/811,678 dated Dec. 9, 2019.
Amendment Response to FOA for U.S. Appl. No. 15/811,678 dated Jun. 11, 2020.
Notice of Allowance for U.S. Appl. No. 15/811,678 dated Nov. 18, 2020.
Notice of Allowance for U.S. Appl. No. 15/811,678 dated Jul. 29, 2020.
Ralph C. Merkle, "On the Security of Multiple Encryption", Communications of the ACM, Jul. 1981, vol. 24, No. 7,3 pages (Year: 1981).
Sefi Cohen Arazi, "Antenna Fundamentals" from https://www.mtiwe.com/?CategoryID=353&ArticleID=163, 2016.
European Search Report dated Feb. 24, 2017 for EP Appln. No. 16202919.3.
Translation of Chinese office action dated Apr. 26, 2021 for Chinese patent application No. 201711120783.7.
English translation of foreign OA issued on Dec. 13, 2021, for Chinese Patent Application No. 201711120783.7.

* cited by examiner

METHOD FOR HEARING SYSTEM COMMUNICATION AND RELATED DEVICES

RELATED APPLICATION DATA

This application is the continuation of U.S. patent application Ser. No. 15/811,678, filed on Nov. 14, 2017, pending, which claims priority to, and the benefit of, European Patent Application No. 16202919.3 filed on Dec. 8, 2016. The entire disclosures of the above applications are expressly incorporated by reference herein.

FIELD

The present disclosure relates to communication in a hearing system comprising a server device and a hearing device system, wherein the hearing device system comprises a hearing device and a user accessory device. In particular, the present disclosure relates to methods and devices for communication in a hearing system.

BACKGROUND

Wireless communication to and from different entities of a hearing system has been increasing in continuation of the developments within wireless communication technology. However, the new technologies entail new challenges for the hearing aid manufacturers in order to secure communication in a hearing system. Wireless communication interfaces of a hearing system desirably use an open standard-based interface. However, this poses many challenges in terms of security. Further, a hearing device is a very small device with strict constraints in terms of computational power, memory space etc.

SUMMARY

There is a need for apparatus, devices and methods for providing improved and effective security for hearing system communication. Further, there is a need for devices and methods reducing the risk of hearing device data being compromised by a third (unauthorized) party.

Accordingly, a method for hearing system communication in a hearing system comprising a server device and a hearing device system comprising a hearing device and a user accessory device with a user application installed thereon is provided. The method comprises: obtaining hearing device data for the hearing device in the server device; securing, e.g. encrypting and/or digitally signing, the hearing device data, e.g. using a first security scheme to obtain a first output; securing, e.g. encrypting and/or digitally signing, the first output, e.g. using a second security scheme to obtain a second output, wherein the second security scheme is optionally different from the first security scheme; transmitting the second output to the user application; validating, e.g. decrypting and/or verifying, the second output in the user application, e.g. using the second security scheme to obtain the first output; transmitting the first output to the hearing device; receiving and validating, e.g. decrypting and/or verifying, the first output in the hearing device, e.g. using the first security scheme to obtain the hearing device data; and optionally operating the hearing device according to the hearing device data. The method may comprise transmitting the first output to the hearing device if validating the second output is successful. The method may comprise not transmitting the first output to the hearing device if validating the second output fails.

A server device for communication in a hearing system comprising the server device and a hearing device system comprising a hearing device and a user accessory device with a user application installed thereon is disclosed. The server device comprises a processing unit configured to: obtain hearing device data for the hearing device; secure, e.g. encrypt and/or digitally sign, the hearing device data using a first security scheme to obtain a first output; secure, e.g. encrypt and/or digitally sign, the first output using a second security scheme to obtain a second output, wherein the second security scheme is different from the first security scheme; and transmit the second output to the user application.

Further, a method for hearing system communication in a hearing system comprising a server device and a hearing device system comprising a hearing device and a user accessory device with a user application installed thereon is provided. The method comprises: obtaining hearing device data for the hearing device in the server device; securing, e.g. encrypting and/or digitally signing, the hearing device data, e.g. using a second security scheme to obtain a second output; transmitting the second output to the user application; validating, e.g. decrypting and/or verifying, the second output in the user application, e.g. using the second security scheme to obtain the hearing device data; securing, e.g. encrypting and/or digitally signing, the hearing device data, e.g. using a first security scheme to obtain a first output, wherein the first security scheme is optionally different from the second security scheme; transmitting the first output to the hearing device; receiving and validating, e.g. decrypting and/or verifying, the first output in the hearing device, e.g. using the first security scheme to obtain the hearing device data; and optionally operating the hearing device according to the hearing device data. The method may comprise transmitting the first output to the hearing device if validating the second output is successful. The method may comprise not transmitting the first output to the hearing device if validating the second output fails.

Also, a user application for communication in a hearing system comprising a server device and a hearing device system comprising a hearing device and a user accessory device with the user application installed thereon is provided, wherein the user application is configured to: receive a second output from the server device; validate, e.g. decrypt and/or verify, the second output in the user application using a second security scheme to obtain hearing device data; secure, e.g. encrypt and/or digitally sign, the hearing device data using a first security scheme to obtain a first output, wherein the first security scheme is different from the second security scheme; and transmit the first output to the hearing device.

It is an important advantage of the present disclosure that secure hearing system communication is provided while at the same time considering the limited computational power of a hearing device. Thus, effective and secure hearing system communication is provided.

A method performed by a hearing system comprising a server device and a hearing device system, the hearing device system comprising a hearing device and a user accessory device with a user application installed thereon, the method includes: obtaining hearing device data for the hearing device in the server device; securing the hearing device data using a first security scheme to obtain a first output; securing the first output using a second security scheme to obtain a second output, wherein the second security scheme is different from the first security scheme; transmitting the second output to the user accessory device; validating, using the user application in the user accessory device, the second output that is associated with the second security scheme to obtain the first output; transmitting the first output to the hearing device; validating, using the hearing device, the first output that is associated with the first security scheme to obtain the hearing device data; and operating the hearing device according to the hearing device data.

Optionally, the first security scheme involves a first key having a first key length, and wherein the act of securing the hearing device data using a first security scheme comprises encrypting the hearing device data with the first key to obtain a first cipher text as at least a part of the first output.

Optionally, the act of securing the hearing device data using a first security scheme comprises digitally signing the hearing device data to obtain a first digital signature as at least a part of the first output.

Optionally, act of securing the first output using a second security scheme comprises digitally signing the first output to obtain a second digital signature as at least a part of the second output.

Optionally, the second security scheme involves a second key having a second key length, and wherein act of securing the first output using a second security scheme comprises encrypting the first output with the second key to obtain a second cipher text as at least a part of the second output.

Optionally, the first key length is shorter than the second key length.

Optionally, the second security scheme involves a key having a key length, and wherein act of securing the first output using a second security scheme comprises encrypting the first output with the key to obtain a cipher text as at least a part of the second output.

Optionally, the hearing device data comprises a hearing device data integrity indicator, the method further comprising verifying, in the hearing device, the hearing device data based on the hearing device data integrity indicator, and wherein the act of operating the hearing device according to the hearing device data is performed if the hearing device data are verified.

Optionally, the first security scheme comprises or is based on a first common secret, and wherein the act of securing the hearing device data and the act of validating the first output are performed based on the first common secret.

Optionally, the second security scheme comprises or is based on a second common secret, and wherein the act of securing the first output and the act of validating the second output are performed based on the second common secret.

Optionally, the first security scheme involves a first primary key and a first secondary key; wherein the first secondary key is different from the first primary key; wherein the act of securing the hearing device data is performed based on the first primary key; and wherein the act of validating the first output is performed based on the first secondary key.

Optionally, the second security scheme involves a second primary key and a second secondary key; wherein the second secondary key is different from the second primary key; wherein the act of securing the first output is performed based on the second primary key; and wherein the act of validating the second output is performed based on the second secondary key.

Optionally, the second security scheme involves a primary key and a secondary key; wherein the secondary key is different from the primary key; wherein the act of securing the first output is performed based on the primary key; and wherein the act of validating the second output is performed based on the secondary key.

A server device for communication in a hearing system comprising the server device and a hearing device system, the hearing device system comprising a hearing device and a user accessory device with a user application installed thereon, wherein the server device comprises a processing unit configured to: obtain hearing device data for the hearing device; secure the hearing device data using a first security scheme to obtain a first output; secure the first output using a second security scheme to obtain a second output, wherein the second security scheme is different from the first security scheme; and transmit the second output to the user accessory device.

A method for communication in a hearing system comprising the server device and a hearing device system, the hearing device system comprising a hearing device and a user accessory device with a user application installed thereon, the method includes: obtaining hearing device data for the hearing device; securing the hearing device data using a first security scheme to obtain a first output; securing the first output using a second security scheme to obtain a second output, wherein the second security scheme is different from the first security scheme; and transmitting the second output to the user accessory device.

Optionally, the security scheme comprises a first key having a first key length, and wherein the act of securing the hearing device data using the security scheme comprises encrypting the hearing device data with the first key to obtain a first cipher text as at least a part of the output.

A method performed by a user accessory device, the user accessory device being a part of a hearing device system having a hearing device, the user accessory device having a user application installed thereon, wherein the hearing device system is configured to communicate with a server device, the server device configured to obtain hearing device data, secure the hearing device data using a first security scheme to obtain a first output, secure the first output using a second security scheme to obtain a second output, the method includes: receiving the second output by the user accessory device; validating, using the user application in the user accessory device, the second output that is associated with the second security scheme to obtain the first output; and transmitting the first output to the hearing device for validation to obtain the hearing device data, wherein the hearing device is operable according to the hearing device data upon validation of the first output. A user accessory device that is a part of a hearing device system having a hearing device, the user accessory device having a user application installed thereon, wherein the hearing device system is configured to communicate with a server device, the server device configured to obtain hearing device data, secure the hearing device data using a first security scheme to obtain a first output, secure the first output using a second security scheme to obtain a second output, the user accessory device of the hearing device system configured to: receive the second output; validate the second output that is associated with the second security scheme to obtain the first output; and transmit the first output to the hearing device for validation to obtain the hearing device data, wherein the hearing device is operable according to the hearing device data upon validation of the first output.

A hearing device system includes the user accessory device, and the hearing device, wherein the hearing device is configured to obtain the first output, and validate the first output to obtain the hearing device data.

A method performed by a user accessory device that is a part of a hearing device system having a hearing device, the user accessory device having a user application installed thereon, the method includes: receiving a secured hearing device data by the user accessory device from a server device; validating, using the user application in the user accessory device, the secured hearing device data to obtain the hearing device data; securing, by the user accessory device, the hearing device data using a first security scheme to obtain an output, wherein the secured hearing device data received from the server device is secured using a second security scheme, and wherein the first security scheme is different from the second security scheme; and transmitting the output to the hearing device for validation in the hearing device, wherein the hearing device is operable according to the hearing device data upon validation of the output.

A user accessory device that is a part of a hearing device system having a hearing device, the user accessory device having a user application installed thereon, the user accessory device having a processing unit configured to: receive a secured hearing device data from a server device; validate, using the user application in the user accessory device, the secured hearing device data to obtain the hearing device data; and secure the hearing device data using a first security scheme to obtain an output, wherein the secured hearing device data received from the server device is secured using a second security scheme, and wherein the first security scheme is different from the second security scheme; wherein the user accessory device is configured to transmit the output to the hearing device for validation in the hearing device, wherein the hearing device is operable according to the hearing device data upon validation of the output.

A program product for a user accessory device that is a part of a hearing device system having a hearing device, the program product having a set of instructions, an execution of which by a processing unit in the user accessory device will cause the user accessory device to perform a method, the method includes: receiving a secured hearing device data by the user accessory device from a server device; validating, using the user application in the user accessory device, the secured hearing device data to obtain the hearing device data; securing, by the user accessory device, the hearing device data using a first security scheme to obtain an output, wherein the secured hearing device data received from the server device is secured using a second security scheme, and wherein the first security scheme is different from the second security scheme; and transmitting the output to the hearing device for validation in the hearing device, wherein the hearing device is operable according to the hearing device data upon validation of the output.

A method performed by a hearing system comprising a server device and a hearing device system, the hearing device system comprising a hearing device and a user accessory device with a user application installed thereon, the method includes: obtaining hearing device data for the hearing device in the server device; securing the hearing device data using a security scheme to obtain an output; transmitting the output to the user accessory device; validating, by the user accessory device, the output that is associated with the security scheme to obtain the hearing device data;

securing the hearing device data using another security scheme to obtain another output, wherein the other security scheme is different from the security scheme; transmitting the other output to the hearing device; validating the other output in the hearing device to obtain the hearing device data; and operating the hearing device according to the hearing device data.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
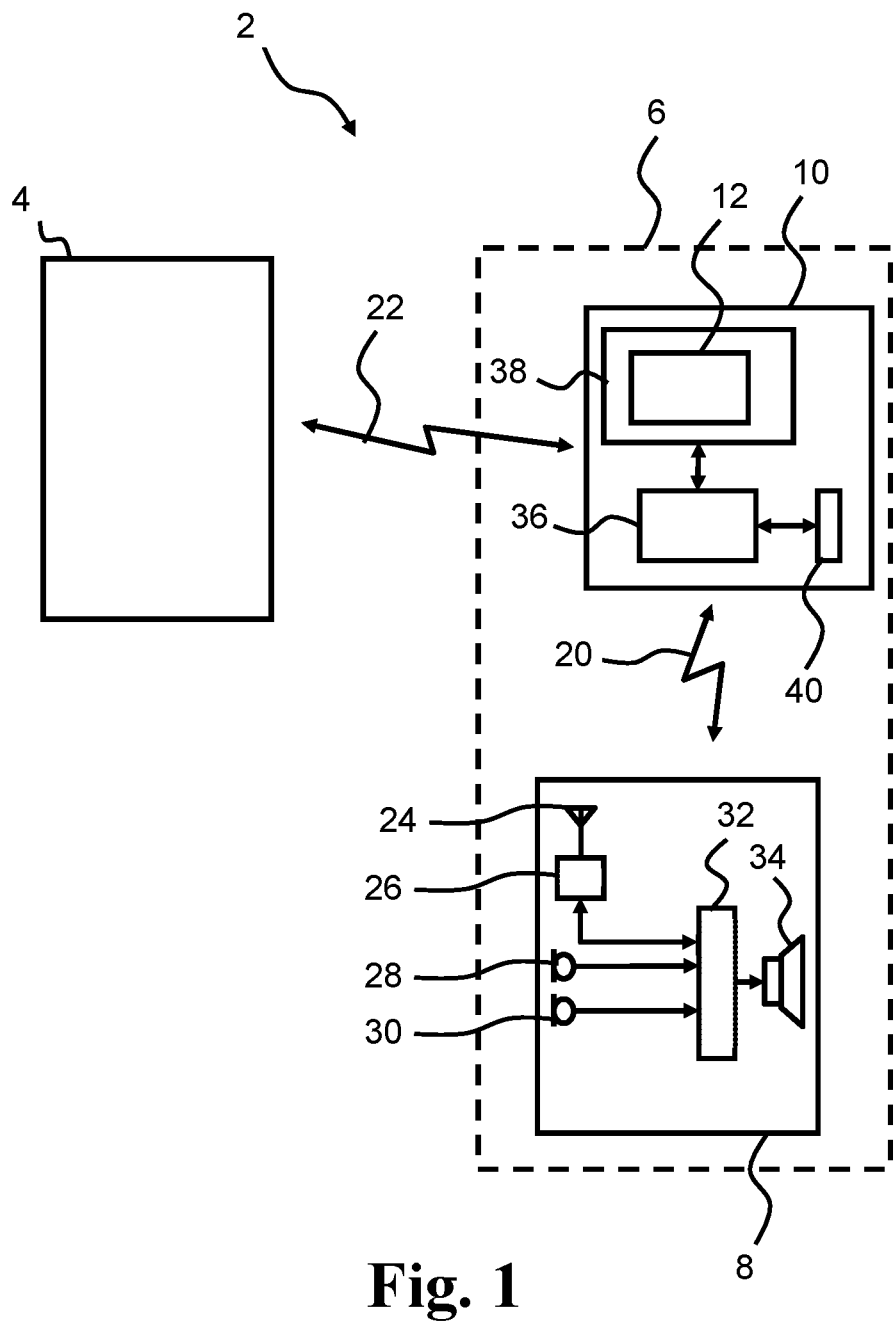
FIG. 1 schematically illustrates a hearing system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The present disclosure relates to improved security in hearing system communication. The hearing system comprises a server device and a hearing device system. The hearing device system comprises a hearing device and a user accessory device having a user application installed thereon. The server device may be controlled by the hearing device manufacturer. The server device may be a distributed server device, i.e. a server device with distributed processors. Namely, the methods, user application and server device disclosed herein enables hearing system communication that is robust against security threats, vulnerabilities and attacks by implementing appropriate safeguards and countermeasures, such as security mechanisms, to protect against threats and attacks. The present disclosure relates to hearing system communication that is robust against replay attacks, unauthorized access, battery exhaustion attacks, and man-in-the-middle attacks.

The user accessory device comprises a memory unit and an interface respectively connected to a processing unit. The memory unit may include removable and non-removable data storage units including, but not limited to, Read Only Memory (ROM), Random Access Memory (RAM), etc. The memory unit has a user application stored thereon. The user application may be a hearing device application, e.g. configured to wirelessly communicate with the hearing device, such as to control and/or configure the hearing device. The interface comprises an antenna and a wireless transceiver, e.g. configured for wireless communication at frequencies in the range from 2.4 to 2.5 GHz. The interface may be configured for communication, such as wireless communication, with the hearing device comprising an antenna and a wireless transceiver.

The present disclosure relates to hearing system communication between entities of a hearing system. The user accessory device forms an accessory device to the hearing device. The user accessory device is typically paired or otherwise wirelessly coupled to the hearing device. The hearing device may be a hearing aid, e.g. of the behind-the-ear (BTE) type, in-the-ear (ITE) type, in-the-canal (ITC) type, receiver-in-canal (RIC) type or receiver-in-the-ear (RITE) type. Typically, the hearing device system is in possession of and controlled by the hearing device user. The user accessory device may be a smartphone, a smartwatch or a tablet computer.

One or more exemplary methods comprise obtaining hearing device data for the hearing device in the server device. The hearing device data may comprise firmware or firmware updates. The hearing device data may comprise hearing device settings for the hearing device. The hearing device data may comprise a hearing device identifier, one or more key identifiers, one or more addresses and/or address identifiers. In one or more exemplary methods, obtaining hearing device data for the hearing device in the server device may comprise receiving hearing device data from a fitting device, e.g. located at a hearing device dispenser. In one or more exemplary methods, obtaining hearing device data for the hearing device in the server device may comprise retrieving hearing device data from a memory, e.g. a database, of the server device.

One or more exemplary methods comprise securing the hearing device data, e.g. using a first security scheme to obtain a first output. The first output may be or comprise a first cipher text being the result of an encryption. One or more exemplary methods comprise securing the hearing device data, e.g. using a second security scheme to obtain a second output. Securing hearing device data may comprise encrypting the hearing device data with a key (first key in first security scheme or second key in second security scheme) to obtain a cipher text (first cipher text in first security scheme or second cipher text in second security scheme). The cipher text obtained by encrypting may be included in the output. Securing hearing device data may comprise digitally signing the hearing device data. The digital signature obtained by digitally signing may be included in the output. Securing the hearing device data using a first security scheme may comprise digitally signing the hearing device data to obtain a first digital signature as at least a part of the first output.

The first security scheme (encrypting and/or digitally signing) may be applied in the server device or in the user application. The second security scheme (encrypting and/or digitally signing) may be applied in the server device. Applying the first security scheme (encrypting and/or digitally signing) in the server device may be advantageous in that the user application does not need to hold encryption keys or any other information about the first security scheme. Further, the hearing device data are encrypted all the way from the server device to the hearing device. Thus, a more secure hearing system communication is provided, since generally the user application is considered less secure than the server device. Further, the required processing power in hearing system communication is reduced for the user application.

A security scheme, such as the first security scheme and/or the second security scheme, may comprise a key, a set of keys or other keying material. A key has a key length. A scheme may comprise a primary key, e.g. used for securing hearing device data/first output, and a secondary key, e.g. used for validating first output/second output. The primary key may be a private (signature) or public (encryption) key. The secondary key may be a private (decryption) or public (verify signature) key.

For example, as a part of securing hearing device data and/or first output, encrypting hearing device data/first output may be based on a primary key being a public key. Further, as a part of validating first output and/or second output, decrypting first output and/or second output (the result of the encryption) may be based on a secondary key being a private key. A security scheme may comprise an encryption algorithm, e.g. a symmetric or asymmetric encryption algorithm, such as Triple DES, RSA, Blowfish, Twofish, Advanced Encryption Standard (AES), and Elliptic Curve Cryptography.

For example, as a part of securing hearing device data and/or first output, digitally signing hearing device data/first output may be based on a primary key being a private key. Further, as a part of validating first output and/or second output, verifying first output and/or second output (the result of digitally signing) may be based on a secondary key being a public key.

In one or more exemplary methods, securing the hearing device data using a second security scheme may comprise digitally signing the hearing device data to obtain a second digital signature as at least a part of the second output.

In one or more exemplary methods, the second security scheme comprises a second key having a second key length, and securing the hearing device data using a second security scheme may comprise encrypting the hearing device data with the second encryption key to obtain a second cipher text as at least a part of the second output.

In one or more exemplary methods, the hearing device data comprises a hearing device data integrity indicator, the method comprising verifying, in the hearing device, the hearing device data based on the hearing device data integrity indicator and operating the hearing device according to the hearing device data if the hearing device data are verified.

One or more exemplary methods may comprise securing the first output using a second security scheme to obtain a second output, e.g. in the server device. The second security scheme is optionally different from the first security scheme.

A scheme, such as the second security scheme, may be different from another scheme, such as the first security scheme, by using keys having different key lengths.

A security scheme may be different from another security scheme if different key lengths are used and/or different keys/key pairs are used. A scheme may be different from another scheme if different encryption algorithms are used in the two schemes. A security scheme may be different from another security scheme if different common secrets are used, i.e. if the first security scheme uses a first common secret and the second security scheme uses a second common secret different from the first common secret. It is an important advantage of the present disclosure that a high server-to-user app security level can be applied in the communication between the server device and the user application/user accessory device, while a power-efficient and/or memory-efficient security level can be applied in the communication between the user application/accessory device and the hearing device. In one or more exemplary methods/devices, the first security scheme may be more complex than the second security scheme i.e. the first security scheme requires more computational power/memory resources to perform than the second security scheme. In one or more exemplary methods/devices, the first security scheme may be less complex than the second security scheme i.e. the first security scheme may less computational power/memory resources to perform than the second security scheme.

One or more exemplary methods comprise transmitting the second output to the user application, e.g. from the server device. The second output may be or comprise a second cipher text being the result of an encryption.

One or more exemplary methods comprise validating the second output in the user application using the second security scheme, e.g. to obtain the first output or the hearing device data. Validating the second output may comprise decrypting a second cipher text of the second output and/or verifying a second digital signature of the second output.

One or more exemplary methods comprise transmitting the first output to the hearing device, e.g. from the user application.

One or more exemplary methods comprises receiving and validating the first output in the hearing device using the first security scheme to obtain the hearing device data. Validating the first output may comprise decrypting a first cipher text of the first output and/or verifying a first digital signature of the first output.

One or more exemplary methods comprise operating the hearing device according to the hearing device data, optionally if validating the first output succeeds or is successful. Operating the hearing device according to the hearing device data may comprise storing at least a part of the hearing device in memory of the hearing device.

The first security scheme may comprise a first encryption key having a first key length. Thus, securing the hearing device data using a first security scheme may comprise encrypting the hearing device data with the first encryption key to obtain a first cipher text as at least a part of the first output.

The second security scheme may comprise a second encryption key having a second key length. Thus, securing the hearing device data or the first output using a second security scheme to obtain a second output may comprise encrypting the hearing device data or the first output with the second encryption key to obtain a second cipher text as at least a part of the second output.

The first key length, also denoted N1, may be shorter or larger than the second key length, also denoted N2. In one or more exemplary methods, the first key length N1 is less than 0.6*N2. In one or more exemplary methods, e.g. where the first security scheme is a symmetric scheme, the first key length is in the range from 50 to 140 bits, such as 128 bits. In one or more exemplary methods, e.g. where the second security scheme is a symmetric scheme, the second key length N2 is larger than 100 bits, such as in the range from 128 to 300 bits, such as 128 bits, 192 bits or 256 bits.

Securing the hearing device data using a first security scheme may comprise digitally signing the hearing device data to obtain a first digital signature as at least a part of the first output.

Securing the first output using a second security scheme may comprise digitally signing the first output to obtain a second digital signature as at least a part of the second output.

The first security scheme may comprise or be based on a first common secret, and securing the hearing device data and validating the first output is optionally based on the first common secret. The first common secret may be based on a hearing device identifier of the hearing device.

The second security scheme may comprise or be based on a second common secret. Securing the hearing device data or the first output and validating the second output is optionally based on the second common secret. The second common secret may be based on the hearing device identifier of the hearing device.

The first security scheme may comprise a first primary key and a first secondary key. The first secondary key may be different from the first primary key. Securing the hearing device data may based on the first primary key and validating the first output may be based on the first secondary key.

The second security scheme may comprise a second primary key and a second secondary key. The second secondary key may be different from the second primary key. Securing the hearing device data or the first output may be based on the second primary key and validating the second output may be based on the second secondary key.

The first security scheme may comprise a first encryption algorithm, and securing the hearing device data using a first security scheme to obtain a first output optionally comprises applying the first encryption algorithm to the hearing device data. The first encryption algorithm may be symmetric, e.g. based on the first common secret. In one or more exemplary methods, the first encryption algorithm is the Advanced Encryption Standard (AES), such as a 128-bit or 196-bit AES.

The second security scheme may comprise a second encryption algorithm optionally different from the first encryption algorithm, and securing the hearing device data or the first output using a second security scheme to obtain a second output optionally comprises applying the second encryption algorithm to the hearing device data or the first output. The second encryption algorithm may be symmetric, e.g. based on the second common secret. In one or more exemplary methods, the second encryption algorithm is the Advanced Encryption Standard (AES), such as a 192-bit AES or a 256-bit AES.

The hearing device data may comprise a hearing device data integrity indicator indicative of hearing device integrity. The hearing device data integrity indicator may be a checksum/hash function. The hearing device data may comprise a digital signature. The method may comprise verifying the hearing device data, e.g. based on the hearing device data integrity indicator and/or the digital signature of the hearing device data, and operating the hearing device according to the hearing device data, optionally if the hearing device data are verified.

Operating the hearing device according to the hearing device data may comprise storing the hearing device data or at least a part thereof in a memory of the hearing device.

Throughout, the same reference numerals are used for identical or corresponding parts.

FIG. 1 shows an exemplary hearing system. The hearing system 2 comprises a server device 4 and a hearing device system 6 comprising a hearing device 8 and a user accessory device 10. The user accessory device 10 is a smartphone configured to wirelessly communicate with the hearing device 8. A user application 12 is installed on the user accessory device 10. The user application may be for controlling the hearing device 8 and/or assisting a hearing device user wearing/using the hearing device 8. In one or more exemplary user applications, the user application 12 is configured to transfer hearing device data, such as firmware and/or hearing device settings, to the hearing device.

The server device 4 and/or the user application 12 may be configured to perform any or some acts of the methods disclosed herein. The hearing device 8 may be configured to compensate for hearing loss of a user of the hearing device 8. The hearing device 8 is configured to communicate with the user accessory device 10/user application 12, e.g. using a wireless and/or wired first communication link 20. The first communication link 20 may be a single hop communication link or a multi-hop communication link. The first communication link 20 may be carried over a short-range communication system, such as Bluetooth, Bluetooth low energy, IEEE 802.11 and/or Zigbee. The first communication link 20 may be carried over a short-range communication system per a proprietary protocol.

In an exemplary hearing system, the hearing device data are secured in the server device using the second security scheme and the first security scheme is then applied to hearing device data in the user application (being the result of validating the second output using the second security scheme in the user application).

The user accessory device 10/user application 12 is configured to connect to the server device 4 over a network, such as the Internet and/or a mobile phone network, via a second communication link 22. The server device 4 may be controlled by the hearing device manufacturer. The hearing device 8 comprises an antenna 24 and a radio transceiver 26 coupled to the antenna 24 for receiving/transmitting wireless communication including first communication link 20. The hearing device 8 comprises a set of microphones comprising a first microphone 28 and optionally a second microphone 30 for provision of respective first and second microphone input signals. The hearing device 8 may be a single-microphone hearing device. The hearing device 8 comprises a memory unit (not shown) connected to the processor, wherein hearing device data, e.g. hearing device settings and/or firmware are stored in the memory unit.

The hearing device 8 comprises a processor 32 connected to the transceiver 26 and microphones 28, 30 for receiving and processing input signals. The processor 32 is configured to compensate for a hearing loss of a user based on hearing device settings and to provide an electrical output signal based on the input signals. A receiver 34 converts the electrical output signal to an audio output signal to be directed towards an eardrum of the hearing device user.

The user accessory device 10 comprises a processing unit 36, a memory unit 38, an interface 40. The user application 12 is installed in the memory unit 38 of the user accessory device 10 and is configured to receive a second output from the server device; validate the second output in the user application using a second security scheme to obtain hearing device data or first output. If the validation with the second security scheme provides hearing device data, the user application is configured to secure the hearing device data using a first security scheme to obtain a first output, wherein the first security scheme is different from the second security scheme. On the other hand, if the hearing device data have already been secured in the server device using a first security scheme, the output of the validation with the second security scheme corresponds to or at least comprises the first output. Subsequently, the user application is configured to transmit the first output to the hearing device.

Figure 2:
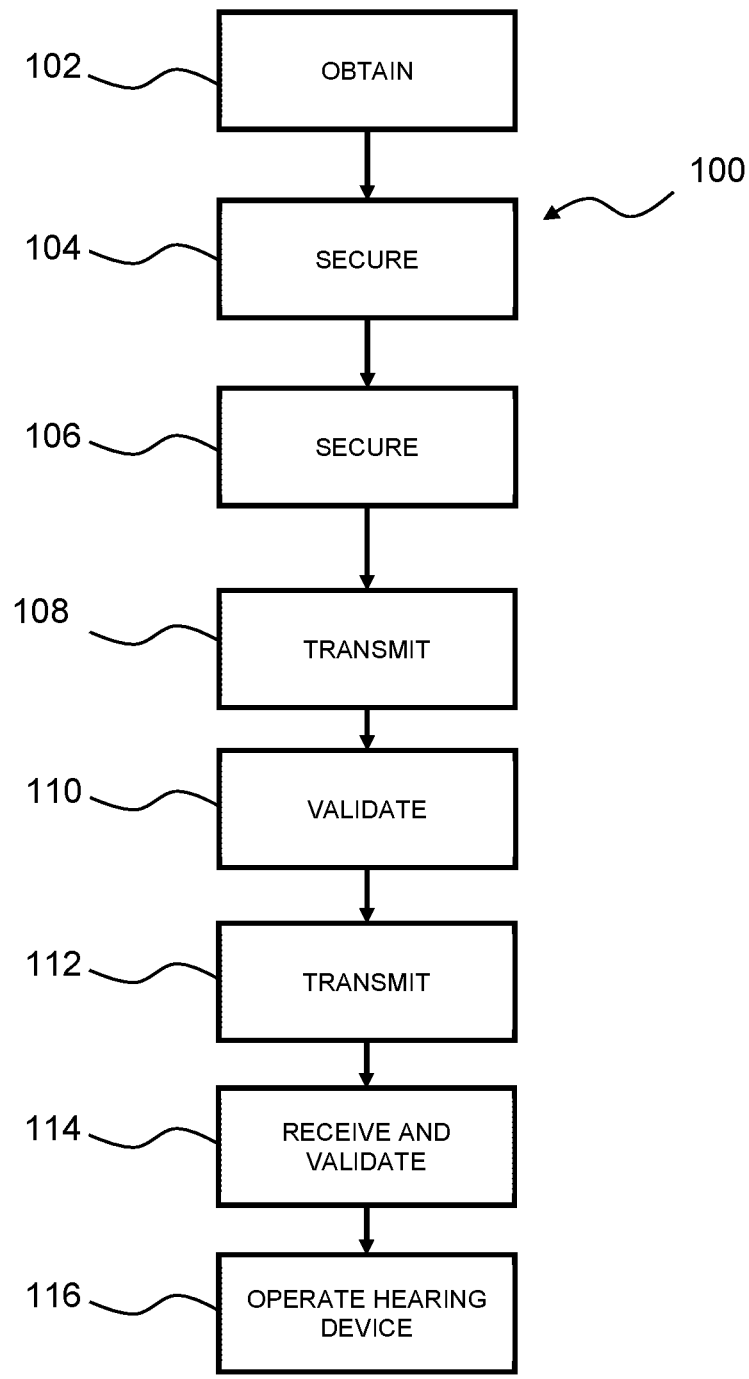
FIG. 2 is a flow diagram of an exemplary method.

FIG. 2 shows an exemplary method for hearing system communication in a hearing system. The method 100 comprises obtaining 102 hearing device data for the hearing device in the server device. The hearing device data may comprise firmware and/or hearing device settings for the hearing device in question. The method 100 comprises securing 104, e.g. digitally signing and/or encrypting, the hearing device data using a first security scheme to obtain a first output in the server device 4; securing 106, e.g. digitally signing and/or encrypting, the first output using a second security scheme to obtain a second output in the server device 4, wherein the second security scheme is different from the first security scheme; transmitting 108 the second output from the server device 4 to the user application 12 of the accessory device 10; validating 110 the second output in the user application using the second security scheme to obtain the first output; transmitting 112 the first output from the user application 12 of the accessory device 10 to the hearing device; receiving and validating 114 the first output in the hearing device using the first security scheme to obtain the hearing device data; and operating 116 the hearing device according to the hearing device data. Operating 116 the hearing device according to the hearing device data may comprise storing hearing device data or at least parts thereof in memory of the hearing device if validating the first output is successful.

Figure 3:
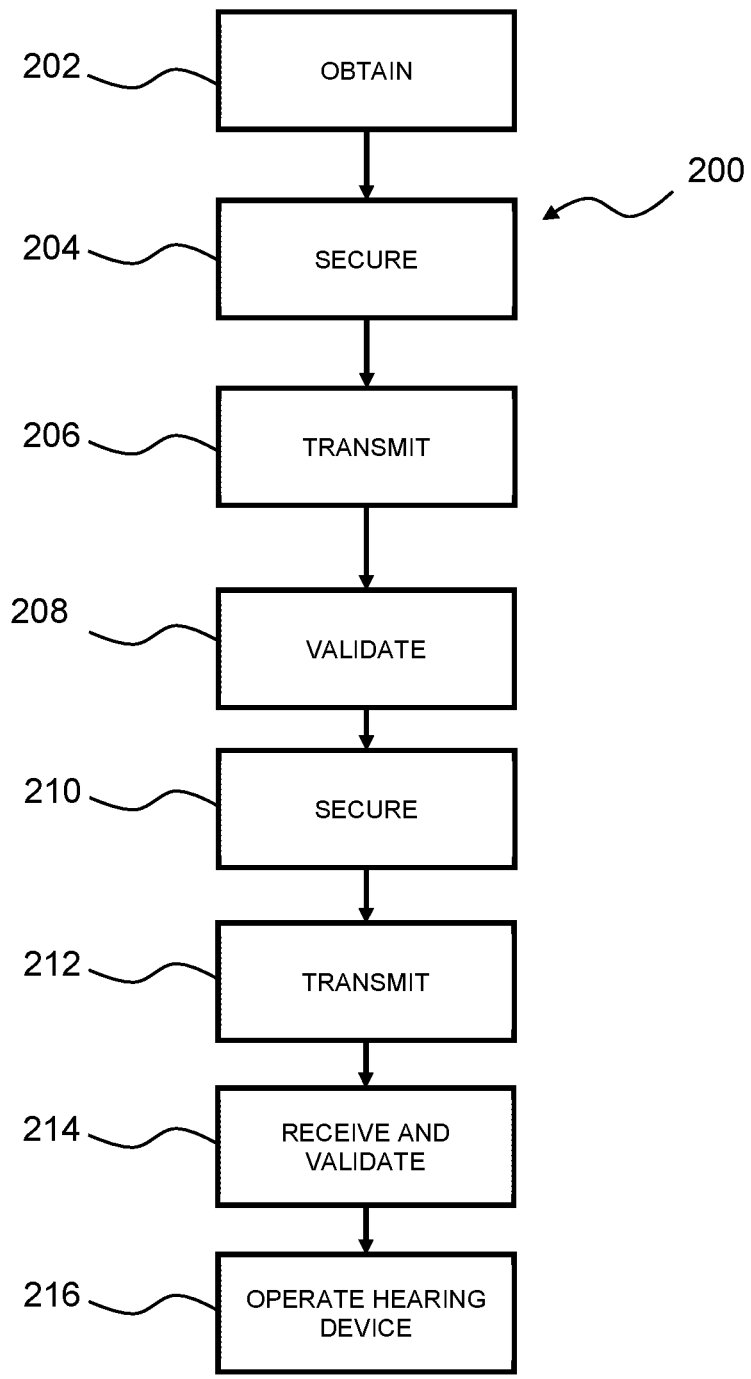
FIG. 3 is a flow diagram of an exemplary method, and
FIG. 4 schematically illustrates an exemplary server device.

FIG. 3 shows an exemplary method for hearing system communication in a hearing system. The method 200 comprises: obtaining 202 hearing device data for the hearing device in the server device; securing 204 in the server device 4 the hearing device data using a second security scheme to obtain a second output; 206 transmitting the second output from the server device 4 to the user application 12 of the accessory device 10; validating 208 the second output in the user application 12 using the second security scheme to obtain the hearing device data; securing 210 by the user application 12 the hearing device data using a first security scheme to obtain a first output, wherein the first security scheme is different from the second security scheme; transmitting 212 the first output from the user application 12 to the hearing device; receiving and validating 214 the first output in the hearing device using the first security scheme to obtain the hearing device data; and operating 216 the hearing device according to the hearing device data. Operating 216 the hearing device according to the hearing device data may comprise storing hearing device data or at least parts thereof in memory of the hearing device if validating the first output is successful.

Figure 4:
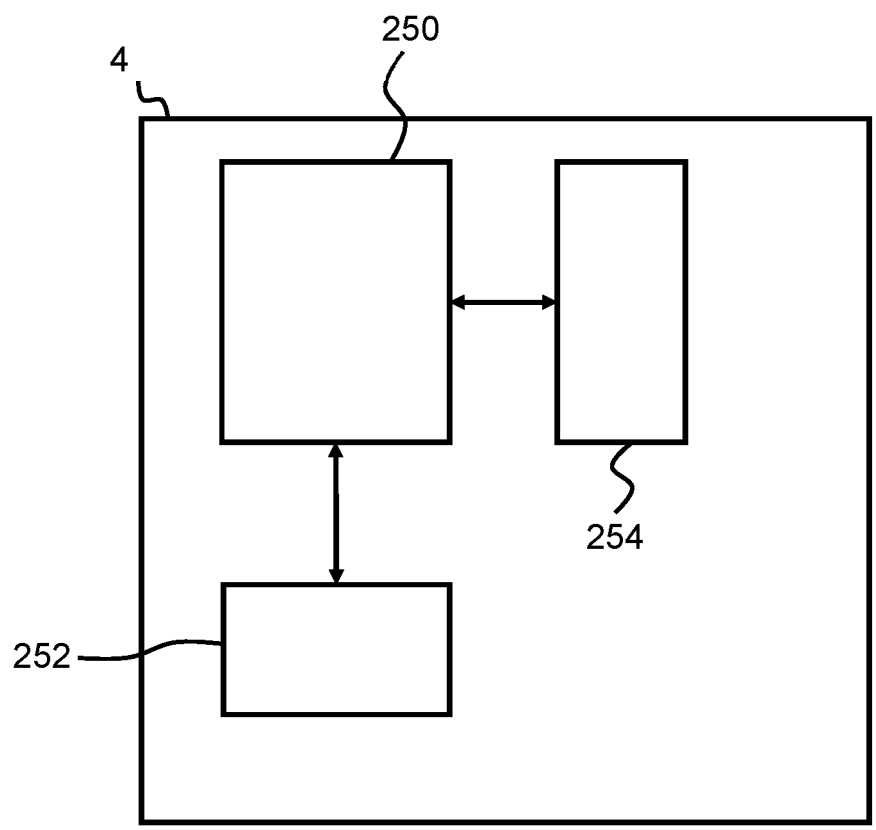

FIG. 4 shows an exemplary server device 4 for communication in a hearing system comprising the server device and a hearing device system comprising a hearing device and a user accessory device with a user application installed thereon. The server device 4 comprises a processing unit 250, e.g. comprising one or more processors, a memory unit 252, e.g. comprising a database, and an interface 254. The processing unit 250 is configured to obtain hearing device data for the hearing device, e.g. from the memory unit 252 and/or via the interface 254 from e.g. a fitting device; secure the hearing device data using a first security scheme to obtain a first output; secure the first output using a second security scheme to obtain a second output, wherein the second security scheme is different from the first security scheme; and transmit the second output to the user application.

The use of the terms "first", "second", "third" and "fourth", etc. does not imply any particular order, but are included to identify individual elements. Moreover, the use of the terms first, second, etc. does not denote any order or importance, but rather the terms first, second, etc. are used to distinguish one element from another. Note that the words first and second are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES 2 hearing system
4 server device
6 hearing device system
8 hearing device
10 user accessory device
12 user application
20 first communication link
22 second communication link
24 antenna
26 radio transceiver
28 first microphone
30 second microphone
32 processor
34 receiver
36 processing unit
38 memory unit
40 interface
100 method for hearing system communication in a hearing system
102 obtain
104 secure
106 secure
108 transmit
110 validate
112 transmit
114 receive and validate
116 operate hearing device
200 method for hearing system communication in a hearing system
202 obtain
204 secure
206 transmit
208 validate
210 secure
212 transmit
214 receive and validate
216 operate hearing device
250 processing unit
252 memory unit
254 interface

The invention claimed is:

1. A server device for communication in a hearing system comprising the server device and a hearing device system, the hearing device system comprising a hearing device and a user accessory device with a user application installed thereon, wherein the server device comprises a processing unit configured to:
obtain hearing device data for the hearing device;
secure the hearing device data using a first security scheme to obtain a first output;
secure the first output using a second security scheme to obtain a second output, wherein the second security scheme is different from the first security scheme; and
transmit the second output to the user accessory device, wherein the second output is processable by the user accessory device to obtain the first output for transmission by the user accessory device to the hearing device.

2. The server device of claim 1, wherein the first output is processable by the hearing device to obtain the hearing device data after the hearing device receives the first output from the user accessory device.

3. The server device of claim 1, wherein the first security scheme involves a first key having a first key length, and wherein the processing unit is configured to secure the hearing device data by encrypting the hearing device data with the first key to obtain a first cipher text as at least a part of the first output.

4. The server device of claim 3, wherein the second security scheme involves a second key having a second key length, and wherein the processing unit is configured to secure the first output by encrypting the first output with the second key to obtain a second cipher text as at least a part of the second output.

5. The server device of claim 4, wherein the first key length is shorter than the second key length.

6. The server device of claim 1, wherein the processing unit is configured to secure the hearing device data by digitally signing the hearing device data to obtain a first digital signature as at least a part of the first output.

7. The server device of claim 6, wherein the processing unit is configured to secure the first output by digitally signing the first output to obtain a second digital signature as at least a part of the second output.

8. The server device of claim 1, wherein the first security scheme comprises or is based on a first common secret, and wherein the processing unit is configured to secure the hearing device data based on the first common secret.

9. The server device of claim 8, wherein the second security scheme comprises or is based on a second common secret, and wherein the processing unit is configured to secure the first output based on the second common secret.

10. The server device of claim 1, wherein the first security scheme involves a first primary key and a first secondary key;
wherein the first secondary key is different from the first primary key;
wherein the processing unit is configured to secure the hearing device data based on the first primary key; and
wherein the first output is configured to be validated by the hearing device based on the first secondary key after the hearing device receives the first output from the user accessory device.

11. The server device of claim 10, wherein the second security scheme involves a second primary key and a second secondary key;
wherein the second secondary key is different from the second primary key;
wherein the processing unit is configured to secure the first output based on the second primary key; and
wherein the second output is configured to be validated based on the second secondary key.

12. The server device of claim 1, wherein the second security scheme involves a primary key and a secondary key;
wherein the secondary key is different from the primary key;
wherein the processing unit is configured to secure the first output based on the primary key; and
wherein the second output is configured to be validated based on the secondary key.

13. The server device of claim 1, wherein the server device is configured to communicate with a fitting device, and to obtain the hearing device data for the hearing device from the fitting device.

14. The server device of claim 1, further comprising a memory, wherein the hearing device data is stored in the memory, and wherein the processing unit of the server device is configured to obtain the hearing device data from the memory of the server device.

15. The server device of claim 1, wherein the hearing device data comprises firmware for the hearing device, wherein the processing unit of the server device is configured to obtain the hearing device data by obtaining the firmware, and wherein the second output comprises double-encrypted firmware for the hearing device.

16. The server device of claim 1, wherein the hearing device data comprises a setting for the hearing device, wherein the processing unit of the server device is configured to obtain the hearing device data by obtaining the setting, and wherein the second output comprises double-encrypted setting for the hearing device.

17. The server device of claim 1, wherein the hearing device data comprises a hearing device identifier for the hearing device, wherein the processing unit of the server device is configured to obtain the hearing device data by obtaining the hearing device identifier, and wherein the second output comprises double-encrypted hearing device identifier for the hearing device.

18. The server device of claim 1, wherein the hearing device data comprises an address identifier for the hearing device, wherein the processing unit of the server device is configured to obtain the hearing device data by obtaining the address identifier, and wherein the second output comprises double-encrypted address identifier for the hearing device.

19. A method for communication in a hearing system comprising a server device and a hearing device system, the hearing device system comprising a hearing device and a user accessory device with a user application installed thereon, the method comprising:
obtaining hearing device data for the hearing device;
securing the hearing device data using a first security scheme to obtain a first output;
securing the first output using a second security scheme to obtain a second output, wherein the second security scheme is different from the first security scheme; and
transmitting the second output to the user accessory device, wherein the second output is processable by the user accessory device to obtain the first output for transmission by the user accessory device to the hearing device.

20. The method according to claim 19, wherein the first security scheme comprises a first key having a first key length, and wherein the act of securing the hearing device data using the first security scheme comprises encrypting the hearing device data with the first key to obtain a first cipher text as at least a part of the first output.

21. A user accessory device that is a part of a hearing device system having a hearing device, the user accessory device having a user application installed thereon, the user accessory device having a processing unit configured to:
receive a secured hearing device data from a server device, wherein the secured hearing device data is based on a first security scheme and is provisioned in the server device;
validate, using the user application in the user accessory device, the secured hearing device data to obtain hearing device data; and
secure the hearing device data using a second security scheme to obtain an output, wherein the first security scheme is different from the second security scheme;
wherein the user accessory device is configured to transmit the output to the hearing device for validation in the hearing device, wherein the hearing device is operable according to the hearing device data upon validation of the output.

22. A hearing device system comprising the user accessory device of claim 21, and the server device, wherein the server device is configured to secure the hearing device data based on the first security scheme.

23. A hearing device system comprising the user accessory device of claim 21, and the hearing device, wherein the hearing device is configured to obtain the output, and validate the output to obtain the hearing device data.

24. The user accessory device of claim 21, wherein one or each of the first and second security schemes involves no more than a single encryption.

25. The user accessory device of claim 21, wherein the secured hearing device data comprises a secured firmware for the hearing device, wherein the processing unit of the user accessory device is configured to validate the secured hearing device data by validating the secured firmware to obtain a firmware for the hearing device, and to secure the hearing device data by securing the firmware using the second security scheme to obtain the output.

26. The user accessory device of claim 21, wherein the secured hearing device data comprises a secured setting for the hearing device, wherein the processing unit of the user accessory device is configured to validate the secured hearing device data by validating the secured setting to obtain a setting for the hearing device, and to secure the hearing device data by securing the setting using the second security scheme to obtain the output.

27. The user accessory device of claim 21, wherein the secured hearing device data comprises a secured hearing device identifier for the hearing device, wherein the processing unit of the user accessory device is configured to validate the secured hearing device data by validating the secured hearing device identifier to obtain a hearing device identifier for the hearing device, and to secure the hearing device data by securing the hearing device identifier using the second security scheme to obtain the output.

28. The user accessory device of claim 21, wherein the secured hearing device data comprises a secured address for the hearing device, wherein the processing unit of the user accessory device is configured to validate the secured hearing device data by validating the secured address to obtain an address for the hearing device, and to secure the hearing device data by securing the address using the second security scheme to obtain the output.

29. A user accessory device that is a part of a hearing device system having a hearing device, the user accessory device having a user application installed thereon, wherein the hearing device system is configured to communicate with a server device, the server device configured to obtain hearing device data, secure the hearing device data using a first security scheme to obtain a first output, secure the first output using a second security scheme to obtain a second output, the user accessory device of the hearing device system configured to:
receive the second output;
validate the second output that is associated with the second security scheme to obtain the first output; and
transmit the first output to the hearing device for validation to obtain the hearing device data, wherein the hearing device is operable according tothe hearing device data upon validation of the first output.

30. A hearing device system comprising the user accessory device of claim 29, and the server device.

31. A hearing device system comprising the user accessory device of claim 29, and the hearing device, wherein the hearing device is configured to obtain the first output, and validate the first output to obtain the hearing device data.

32. The user accessory device of claim 29, wherein the hearing device data comprises a firmware, wherein the first output comprises a first encrypted firmware, wherein the second output comprises a second encrypted firmware, and wherein the accessory device is configured to validate the second output by validating the second encrypted firmware, and transmit the first output by transmitting the first encrypted firmware to the hearing device for validation to obtain the firmware.

33. The user accessory device of claim 29, wherein the hearing device data comprises a setting, wherein the first output comprises a first encrypted setting, wherein the second output comprises a second encrypted setting, and wherein the accessory device is configured to validate the second output by validating the second encrypted setting, and transmit the first output by transmitting the first encrypted setting to the hearing device for validation to obtain the setting.

34. The user accessory device of claim 29, wherein the hearing device data comprises a hearing device identifier, wherein the first output comprises a first encrypted hearing device identifier, wherein the second output comprises a second encrypted hearing device identifier, and wherein the accessory device is configured to validate the second output by validating the second encrypted hearing device identifier, and transmit the first output by transmitting the first encrypted hearing device identifier to the hearing device for validation to obtain the hearing device identifier.

35. The user accessory device of claim 29, wherein the hearing device data comprises an address, wherein the first output comprises a first encrypted address, wherein the second output comprises a second encrypted address, and wherein the accessory device is configured to validate the second output by validating the second encrypted address, and transmit the first output by transmitting the first encrypted address to the hearing device for validation to obtain the address.

36. A method performed by a user accessory device that is a part of a hearing device system having a hearing device, the user accessory device having a user application installed thereon, the method comprising:
  receiving a secured hearing device data by the user accessory device from a server device, wherein the secured hearing device data is based on a first security scheme, and is provisioned in the server device;
  validating, using the user application in the user accessory device, the secured hearing device data to obtain hearing device data;
  securing, by the user accessory device, the hearing device data using a second security scheme to obtain an output, wherein the first security scheme is different from the second security scheme; and
  transmitting the output to the hearing device for validation in the hearing device, wherein the hearing device is operable according to the hearing device data upon validation of the output.

37. The method of claim 36, wherein one or each of the first and second security schemes involves no more than a single encryption.

38. The method of claim 36, wherein the secured hearing device data comprises a secured firmware for the hearing device, wherein the act of validating the secured hearing device data comprises validating the secured firmware to obtain a firmware for the hearing device, and wherein the act of securing the hearing device data comprises securing the firmware using the second security scheme to obtain the output.

39. The method of claim 36, wherein the secured hearing device data comprises a secured setting for the hearing device, wherein the act of validating the secured hearing device data comprises validating the secured setting to obtain a setting for the hearing device, and wherein the act of securing the hearing device data comprises securing the setting using the second security scheme to obtain the output.

40. The method of claim 36, wherein the secured hearing device data comprises a secured hearing device identifier for the hearing device, wherein the act of validating the secured hearing device data comprises validating the secured hearing device identifier to obtain a hearing device identifier for the hearing device, and wherein the act of securing the hearing device data comprises securing the hearing device identifier using the second security scheme to obtain the output.

41. The method of claim 36, wherein the secured hearing device data comprises a secured address for the hearing device, wherein the act of validating the secured hearing device data comprises validating the secured address to obtain an address for the hearing device, and wherein the act of securing the hearing device data comprises securing the address using the second security scheme to obtain the output.

42. A method performed by a user accessory device, the user accessory device being a part of a hearing device system having a hearing device, the user accessory device having a user application installed thereon, wherein the hearing device system is configured to communicate with a server device, the server device configured to obtain hearing device data, secure the hearing device data using a first security scheme to obtain a first output, secure the first output using a second security scheme to obtain a second output, the method comprising:
  receiving the second output by the user accessory device;
  validating, using the user application in the user accessory device, the second output that is associated with the second security scheme to obtain the first output; and
  transmitting the first output to the hearing device for validation to obtain the hearing device data, wherein the hearing device is operable according to the hearing device data upon validation of the first output.

43. The method of claim 42, wherein the hearing device data comprises a firmware, wherein the first output comprises a first encrypted firmware, wherein the second output comprises a second encrypted firmware, wherein the act of validating the second output comprises validating the second encrypted firmware, and wherein the act of transmitting the first output comprises transmitting the first encrypted firmware to the hearing device for validation to obtain the firmware.

44. The method of claim 42, wherein the hearing device data comprises a setting, wherein the first output comprises a first encrypted setting, wherein the second output comprises a second encrypted setting, wherein the act of validating the second output comprises validating the second encrypted setting, and wherein the act of transmitting the first output comprises transmitting the first encrypted setting to the hearing device for validation to obtain the setting.

45. The method of claim 42, wherein the hearing device data comprises a hearing device identifier, wherein the first output comprises a first encrypted hearing device identifier, wherein the second output comprises a second encrypted hearing device identifier, wherein the act of validating the second output comprises validating the second encrypted hearing device identifier, and wherein the act of transmitting the first output comprises transmitting the first encrypted hearing device identifier to the hearing device for validation to obtain the hearing device identifier.

46. The method of claim 42, wherein the hearing device data comprises an address, wherein the first output comprises a first encrypted address, wherein the second output comprises a second encrypted address, wherein the act of validating the second output comprises validating the second encrypted address, and wherein the act of transmitting the first output comprises transmitting the first encrypted address to the hearing device for validation to obtain the address.

* * * * *